United States Patent [19]

Smith et al.

[11] Patent Number: 4,657,710
[45] Date of Patent: Apr. 14, 1987

[54] VAPORIZERS

[75] Inventors: John M. Smith, Keighley; James J. Miles, Wilmslow, both of England

[73] Assignee: The BOC Group plc, Windlesham, England

[21] Appl. No.: 660,616

[22] Filed: Oct. 15, 1984

[30] Foreign Application Priority Data

Nov. 19, 1983 [GB] United Kingdom ................. 8330948

[51] Int. Cl.⁴ .......................... B01D 47/00; C10J 1/00; C10K 1/08; F24M 3/14
[52] U.S. Cl. .............................. 261/46; 261/DIG. 65; 261/DIG. 74
[58] Field of Search ............. 261/45, 46, 47, DIG. 65, 261/DIG. 74

[56] References Cited

U.S. PATENT DOCUMENTS

| 2,968,474 | 1/1961 | Eichelman et al. | 261/46 |
| 3,319,945 | 5/1967 | Person | 261/46 |
| 4,436,674 | 3/1984 | McMenamin | 261/DIG. 65 |

Primary Examiner—Edward G. Favors
Attorney, Agent, or Firm—Roger M. Rathbun; Larry R. Cassett

[57] ABSTRACT

A vaporizer includes means 11 which may be an electronically controlled solenoid valve to divert repeatedly a carrier gas into either a first path which goes directly from the inlet 3 to the outlet 5 of the vaporizer or a second path which enters a vaporizing chamber 13 to entrain volatile liquid vapor before re-joining the first path.

6 Claims, 3 Drawing Figures

% ON TIME
= $W/T \times 100$
= $0.25 \times 100$
= $25\%$

VAPORIZERS

BACKGROUND OF THE INVENTION

The present invention relates to vaporisers and in particular to vaporisers for medical purposes.

Frequently, volatile liquid agents need to be administered to patients in vapour form for a variety of medical purposes. For example, anaesthetic vaporisers are devices for mixing the vapour of a volatile liquid anaesthetic agent with a carrier gas (which term is to be understood to include gas mixtures) for subsequent administration to a patient.

Anaesthetic vaporisers are known in which the carrier gas supplied to the vaporiser is divided into two streams. One stream is directed through a vaporising chamber where it becomes enriched with the vapour of the anaesthetic. The second stream by-passes the vaporising chamber. The two streams subsequently reunite downstream of the vaporising chamber and then pass through an outlet of the vaporiser for administration to the patient.

Such anaesthetic vaporisers are know generally as "by-pass" vaporisers and the concentration of anaesthetic vapour in the gas leaving the vaporiser is frequently controlled by mechanical means such as thermally sensitive valve arrangements and restrictor valves placed in one or both of the streams.

Such valve arrangements frequently require very accurate machining and calibration and although effective are extremely expensive to manufacture. Furthermore, known valve arrangements have tended to be large and heavy.

SUMMARY OF THE INVENTION

It is an aim of the present invention to provide a vaporiser which is simple to manufacture and offers the advantage of being suitable for recorder output.

According to the present invention, a vaporiser comprises a vaporising chamber for volatile liquid to be vaporised, and inlet for carrier gas, an outlet for carrier gas and vapour and means for repeatedly diverting the carrier gas either along a first path which by-passes the vaporising chamber or a second path which passes through the vaporising chamber for entraining vapour of the volatile liquid.

Preferably, prior to reaching said means, the carrier gas is initially divided into a main bypass stream for flow directly from the inlet to the outlet and a stream for flow towards said means. Preferably, said means is an electronically controlled solenoid valve.

BRIEF DESCRIPTION OF DRAWINGS

Embodiments of the invention will now be described by way of example, reference being made to the Figures of the accompanying diagrammatic drawings in which:

As shown in FIG. 1 an anaesthetic vaporiser 1 has an inlet 3 for a carrier gas, for example, oxygen and an outlet 5 from which carrier gas and anaesthetic vapour can leave the vaporiser for delivery to a patient. The carrier gas is initially divided into two streams, namely a main by-pass stream which passes directly from inlet 3 towards outlet 5 along a conduit 4 and a further stream which passes along a conduit 6 towards means in the form of an electronically controlled three-way solenoid valve 11. The proportion of carrier gas in the main by-pass stream and further stream are controlled by means in the form of flow splitters 7 and 9.

Figure 1:
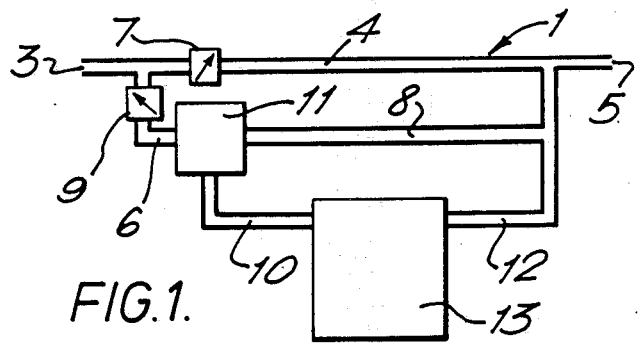
FIG. 1 is a schematic flow diagram illustrating the flow of carrier gas through an anaesthetic vaporiser according to the present invention.

The further stream flow along conduit 6 until it reaches the three-way solenoid valve 11, after which it is diverted into either a first path including a passageway 8 which by-passes a vaporising chamber 13 or a second path including a passageway 10 communicating with the vaporising chamber 13. A passageway 12 extends between the vaporising chamber 13 and the outlet 5 for the passage therethrough of carrier gas and anaesthetic vapour. The passageways 4, 8 and 12 all communicate upstream of the outlet 5.

Figure 2:
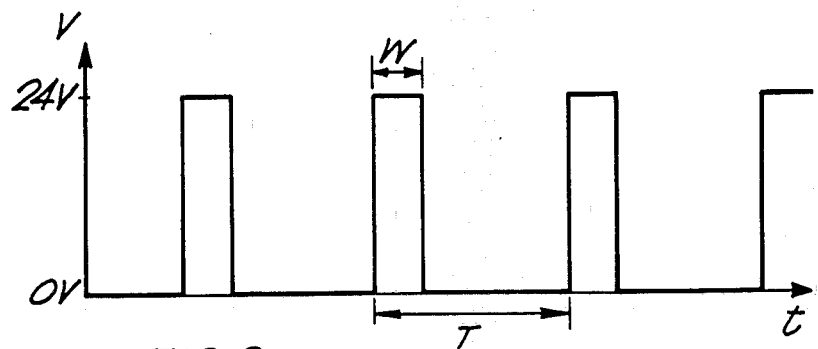
FIG. 2 is a graph of voltage against time illustrating the pulsed power supply to the solenoid valve of FIG. 1

The soleoid valve 11 is electronically controlled and the power supply to the directional valve 11 is 24 vdc driven by a pulse generator through a transistor. Pulse width and period are controlled using conventional electronic methods. Referring to FIG. 2, the solenoid valve is triggered to divert carrier gas towards the vaporising chamber 13 along passageway 10 at, for example, a rate of once per second for a variable period W which for example may be 25% of the period between pulses.

In operation, carrier gas enters the anaesthetic vaporiser 1 at inlet 3 and according to the setting of the stream splitters 7, 9 a major portion will flow through passageway 4 towards outlet 5. However, a proportion which can be varied but may be, for example, 10% by volume of the carrier gas will be directed through passageway 6 towards solenoid valve 11. The solenoid valve 11 is pulsed at an appropriate drate. This may be approximately once per second and diverts the carrier gas along either said first or second paths in for example the ratio of one quarter towards the vaporising chamber 13 and three quarters through the passageway 8 towards the outlet 5. Carrier gas flowing along the second path passes through passageway 10, through vaporising chamber 13 and carrier gas and anaesthetic vapour then pass through passageway 12 to join with the carrier gas flowing along the first path and the main by-pass stream before leaving the anaesthetic vaporiser 1 via outlet 5. It should be understood that the proportion of the carrier gas flow directed through passageway 6 may be varied to suit the physical characteristics of the anaesthetic agent and the maximum concentration required for the vaporiser.

The switching of solenoid valve 11 determines the output concentration, together with other relevant parameters e.g. the flow ratio determined by the stream splitter 7, 9, the vaporising chamber efficiency etc. The switching of the valve may be varied either in terms of pulse width or frequency or both in order to deliver the required concentration.

The circuitry controlling the switching may include inputs from various sensors to correct for the effects of e.g. vaporising chamber temperature, room temperature, gas temperature, gas composition, gas flowrate, back pressure, liquid level etc. The control circuitry may also accept external inputs from devices monitoring clinical parameters such as circuit concentrations, inspired concentration, end-tidal concentration etc.

Depending upon the output concentration required, the control circuitry may produce a varying pulse shape to achieve enhanced valve response.

The above described embodiment has the advantage that calibration of the anaesthetic vaporiser is derived from electronic timing methods rather than precision valves which are extremely difficult to manufacture and calibrate accurately. Further, there are few moving parts and the overall size and weight of the vaporiser can be reduced as compared to prior art vaporisers. An added advantage is that the anaesthetic vaporiser is eminently suited for recorder output and for control from a remote source.

Figure 3:
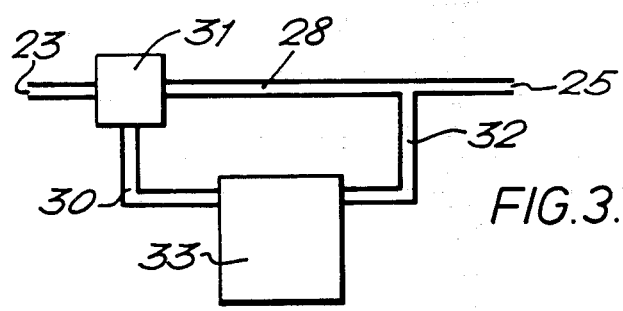
FIG. 3 is a schematic flow diagram of a further embodiment of an anaesthetic vaporiser of the present invention.

In a second embodiment as shown in FIG. 3, the main by-pass stream is in substance omitted so that the carrier gas entering inlet 23 immediately passes to solenoid valve 31 which diverts it either along a first path including a passageway 28 towards outlet 25 or a second path including a passage 30 towards a vaporising chamber 33. A passage 32 connects the vaporising chamber to the passageway 28 in order that carrier gas and anaesthetic vapour in the second path can be reunited with the carrier gas in the first path before leaving the vaporiser at outlet 25.

As with the previous example, the solenoid valve is powered by pulses which repeatedly divert the carrier gas from the first path to the second path and vice-versa.

It has been found that the embodiment illustrated in FIG. 1 can be used over a concentration range more suitable for anaesthetics than the embodiment illustrated in FIG. 3.

Although reference has been made in the embodiments described above to anaesthetic vaporisers, clearly the vaporisers could be adapted to administer volatile agents for non-anaesthetic purposes, for example, the treatment of asthma.

In a modification, the solenoid valve 11, 31 could be positioned downstream of its associated vaporising chamber 13, 33. Similarly, with regard to the flow splitter 9, thus could also be positioned downstream of vaporising chamber 13.

Although reference has been made in the above described embodiments to solenoid valves, any means capable of diverting repeatedly the carrier gas along either the first or second paths could be used. For example such a means could be in the form of a fluidic timing device or an electrical device.

We claim:

1. A vaporisor comprising a vaporising chamber for volatile liquid to be vaporised, an inlet for carrier gas, an outlet for carrier gas and vapour and means for diverting repeatedly the total flow of the carrier gas either along a first path which by-passes the vaporising chamber or a second path which passes through the vaporising chamber for entraining vapour of the volatile liquid and means for controlling automatically said diverting means to vary the output concentration of the vapour of the volatile liquid in the carrier gas.

2. A vaporiser as claimed in claim 1, in which prior to reaching said means, the carrier gas is initially divided into a main by-pass stream for flow directly from the inlet to the outlet and a further stream for flow towards said means.

3. A vaporiser as claimed in claim 2, in which further means is provided for varying the ratio by volume of carrier gas in the main by-pass stream to the further stream flowing towards said diverting means.

4. A vaporiser as claimed in claim 1, in which said diverting means is a solenoid valve.

5. A vaporizer as claimed in claim 4 including electronic means to control the switching of said solenoid valve to vary the output concentration of the vapor of the volatile liquid which passes through the outlet.

6. A vaporiser as claimed in claim 4, in which the solenoid valve is positioned upstream of the vaporising chamber.

* * * * *